United States Patent
Smith et al.

(10) Patent No.: US 7,261,723 B2
(45) Date of Patent: Aug. 28, 2007

(54) SURGICAL INSTRUMENT AND METHOD FOR THE TREATMENT OF URINARY INCONTINENCE

(75) Inventors: Daniel J. Smith, Dayton, NJ (US); Jonathan B. Gabel, Randolph, NJ (US); Henri A. M. Decloux, Herve (BE)

(73) Assignee: Ethicon, Inc., Somerville, NJ (US)

( * ) Notice: Subject to any disclaimer, the term of this patent is extended or adjusted under 35 U.S.C. 154(b) by 636 days.

(21) Appl. No.: 10/706,559

(22) Filed: Nov. 12, 2003

(65) Prior Publication Data

US 2005/0101973 A1  May 12, 2005

(51) Int. Cl.
*A61F 2/04* (2006.01)
*A61B 17/12* (2006.01)

(52) U.S. Cl. .................. 606/139; 606/119; 600/30; 600/37

(58) Field of Classification Search .................. 606/99, 606/119, 139, 141, 148, 193, 222–227; 600/30, 600/37; 604/544
See application file for complete search history.

(56) References Cited

U.S. PATENT DOCUMENTS

| | | | |
|---|---|---|---|
| 6,024,690 A * | 2/2000 | Lee et al. ................ | 600/3 |
| 6,638,211 B2 | 10/2003 | Suslian et al. | |
| 6,641,525 B2 * | 11/2003 | Rocheleau et al. ........ | 600/30 |
| 6,752,081 B2 * | 6/2004 | Callahan et al. ........ | 101/484 |

| | | |
|---|---|---|
| 2002/0055748 A1 | 5/2002 | Gellman et al. |
| 2002/0156489 A1 | 10/2002 | Gellman et al. |

FOREIGN PATENT DOCUMENTS

| | | |
|---|---|---|
| EP | 1 342 450 A1 | 9/2003 |
| WO | WO 2004/008877 A1 | 1/2004 |

OTHER PUBLICATIONS

Nickel, R.F. et al., "Evaulation of a Transpelvic Sling Procedure With and Without Colposuspension for Treatment of Female Dogs With Refractory Urethral Sphincter Mechanism Incompetence," Veterinary Surgery 27:94-101 (1998).
International Search Report dated May 17, 2005, for corresponding international application PCT/US2004/036701.

* cited by examiner

*Primary Examiner*—Glenn K. Dawson
*Assistant Examiner*—Kathleen Sonnett

(57) ABSTRACT

A surgical assembly is provided including a surgical passer having a wire portion coupled to a handle, with the wire portion having a free distal end, an outer periphery, and at least one recess therein in a distal end region. The assembly further includes a tube element having a proximal end, a tissue penetrating distal end, and a channel extending therein from an opening at the proximal end and defined by an inner periphery. The channel has at least one projection projecting outwardly into the channel in a distal end region thereof. The outer periphery of the surgical passer is dimensioned relative to the inner periphery of the channel of the tube element so that the surgical passer is positionable within the tube element, and when so positioned, the at least one tube element projection engages the at least one surgical passer recess to removably couple the surgical passer to the tube element.

20 Claims, 7 Drawing Sheets

SURGICAL INSTRUMENT AND METHOD FOR THE TREATMENT OF URINARY INCONTINENCE

BACKGROUND OF THE INVENTION

1. Field of the Invention

The present invention relates generally to devices and methods for the treatment of female urinary incontinence, and more particularly, to an improved surgical instrument and method that can be used to place a sub-urethral sling.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for treating female urinary stress incontinence is described in detail in U.S. Pat. No. 5,899,909, which is incorporated herein by reference in its entirety. This patent discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support around the mid urethra.

Sub-urethral slings have also been place by a different approach, wherein a needle is passed first though the abdominal wall, along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has also been recently developed in which the implanted sling extends from beneath the urethra, and out through the obturator hole on either side. This "transobturator" procedure may involve inserting an appropriately configured needle from a vaginal incision and subsequently out through the obturator hole, or vice versa. The former technique (an "inside-out" approach) will be described in greater detail below, and has been performed using a surgical instrument substantially similar to that shown in FIG. 1. The surgical instrument 100 includes two surgical passers 101, 103 that are secured at a proximal end to handles 102, 104. The surgical passers are curved and form a somewhat helical shape, and are mirror images of one another so that one is particularly suited for passage through the body on one side of the urethra, whereas the other is particularly suited for passage on the opposite side of the urethra. Applied over the ends of the passers are tube elements 106, 108, proximal ends 109 of which are coupled to a tape 110 to be implanted. The tape is preferably of knitted mesh construction, such as Prolene® polypropylene mesh (manufactured by Ethicon, Inc. of Somerville, N.J.) having dimensions of approximately ½×18 inches. The tape is also preferably covered by a plastic sheath that overlaps in the middle section so as to be easily removable.

Previously, the tube elements were secured to the passers to enable passing of the tape into the body by press fitting the tube element onto the distal end of the passer. This attachment method does not allow pre-assembly (assembly prior to use), as sterilization gases (such as ethylene oxide) cannot effectively penetrate into the distal region of the passer and tube beyond where they are press-fit together. Pre-assembly is desirable to avoid product damage due to handling by hospital personnel, to best prevent multiple loose components on the surgical table, and also to prevent or reduce the risk of glove puncture by the sharp tips of the instrument. Further, even if effective sterilization was possible, because the tube element is preferably made of plastic, and would be subject to creep resulting from the constant pressure if pre-assembled, and may also be subject to stress cracking. Finally, manufacturing variations and moisture can have significant affects on press-fit components Thus, it would be desirable to provide an improved surgical assembly in which the surgical passer and tube element are secured together in a manner that enables pre-assembly, allows sterilization of the pre-assembled product, and is not subject to the other issues described above in conjunction with press-fit components.

SUMMARY OF THE INVENTION

The present invention provides a surgical assembly including a surgical passer having a wire portion coupled to a handle, with the wire portion having a free distal end, an outer periphery, and at least one recess therein in a distal end region. The assembly further includes a tube element having a proximal end, a tissue penetrating distal end, and a channel extending therein from an opening at the proximal end and defined by an inner periphery. The channel has at least one projection projecting outwardly into the channel in a distal end region thereof. The outer periphery of the surgical passer is dimensioned relative to the inner periphery of the channel of the tube element so that the surgical passer is positionable within the tube element, and when so positioned, the at least one tube element projection engages the at least one surgical passer recess to removably couple the surgical passer to the tube element.

According to one embodiment, there is substantially no interference between the surgical passer and tube element other than from the at least one tube element projection. In yet another embodiment, the at least one projection is sufficiently smaller than the corresponding recess so as to allow sterilization gas present within the channel to freely pass into a region of the channel distal of the at least one projection. The at least one recess may have a depth of at least approximately 0.05 mm, and the at least one projection may have a height of at least approximately 0.1 mm. In yet another embodiment, the at least one recess and the at least one projection may have a radius of at least approximately 0.1 mm and the at least one projection has a radius of at least approximately 0.1 mm.

The surgical passer may be made of stainless steel and the tube element may be made of a medical grade plastic selected from the group consisting of urethane, polyethylene, and polypropylene.

In yet another embodiment, the leading edge of the surgical passer has a radius of at least 0.1 mm, and in an alternate embodiment, the leading edge of the surgical passer is chamfered.

In another embodiment, the at least one recess is between 0.5 and 120 mm proximal of the distal end of the surgical passer.

The recess of the surgical assembly may be a single recess extending around a circumference of the surgical passer, and the at least one projection may be a single projection extending around the diameter of the channel. In an alternate embodiment, the at least recess is a single recess extending around a circumference of the surgical passer, and the at least one projection is a plurality of projections spaced apart about the diameter of the channel.

In yet another embodiment, the wire portion of the surgical passer has a contour, and the tube element is configured to follow said surgical passer contour. In one embodiment, the curved portion contour is substantially helical.

A surgical assembly for use in implanting a tape to treat female urinary incontinence is also provided including a surgical passer having a wire portion coupled to a handle, at least a portion of the wire portion having a curved contour, a free distal end, an outer periphery, and having at least one recess therein in a distal end region. The assembly further includes a tube element having a proximal end coupled to the tape to be implanted, a tissue penetrating distal end, and a channel extending therein from an opening at the proximal end, the channel having an inner periphery and having at least one projection projecting outwardly into the channel in a distal end region thereof. The tube element has a configuration such that it can be removably positioned over the distal end of the surgical passer and has a contour that substantially follows the contour of the surgical passer. When the tube element is removably positioned over the distal end of the surgical passer, the at least one projection on the surgical passer engages the at least one recess in the tube element.

In one embodiment, there is substantially no interference between the surgical passer and the tube element other than from the at least one tube element projection. In yet another embodiment, the at least one projection is sufficiently smaller than the corresponding recess so as to allow sterilization gas present within the channel to pass freely into a region of the channel distal of the at least one projection. In yet another embodiment, the at least one recess further has a depth of approximately 0.05 mm to 1.0 mm, and the at least one projection has a height of approximately 0.1 to 0.5 mm. The at least one recess may be a single recess extending around a circumference of the surgical passer, and the at least one projection is a single projection extending around the diameter of the channel. In an alternate embodiment, the at least recess is a single recess extending around a circumference of the surgical passer, and the at least one projection is a plurality of projections spaced apart about the diameter of the channel.

Also provided is a surgical assembly for implanting a surgical element within a patient's body that includes a surgical passer having a wire portion coupled to a handle, at least a portion of the wire portion having a curved contour, having a free distal end, an outer periphery, and having at least one recess therein in a distal end region. The assembly also includes a tube element having a proximal end coupled to the tape to be implanted, a tissue penetrating distal end, and a channel extending therein from an opening at the proximal end. The channel has an inner periphery and a means for engaging the at least one recess in the tube element to removably couple the tube element to the surgical passer. The means for engaging is capable of withstanding a removal force of approximately 1 to 10 pounds, but allowing sterilization gas present within the channel to freely pass through to the distal end of the channel.

In one embodiment, the means for engaging is at least one projection projecting outwardly into the tube element channel. In yet another embodiment, the surgical passer is made of stainless steel and the tube element is made of a medical grade plastic selected from the group consisting of urethane, polyethylene, and polypropylene.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
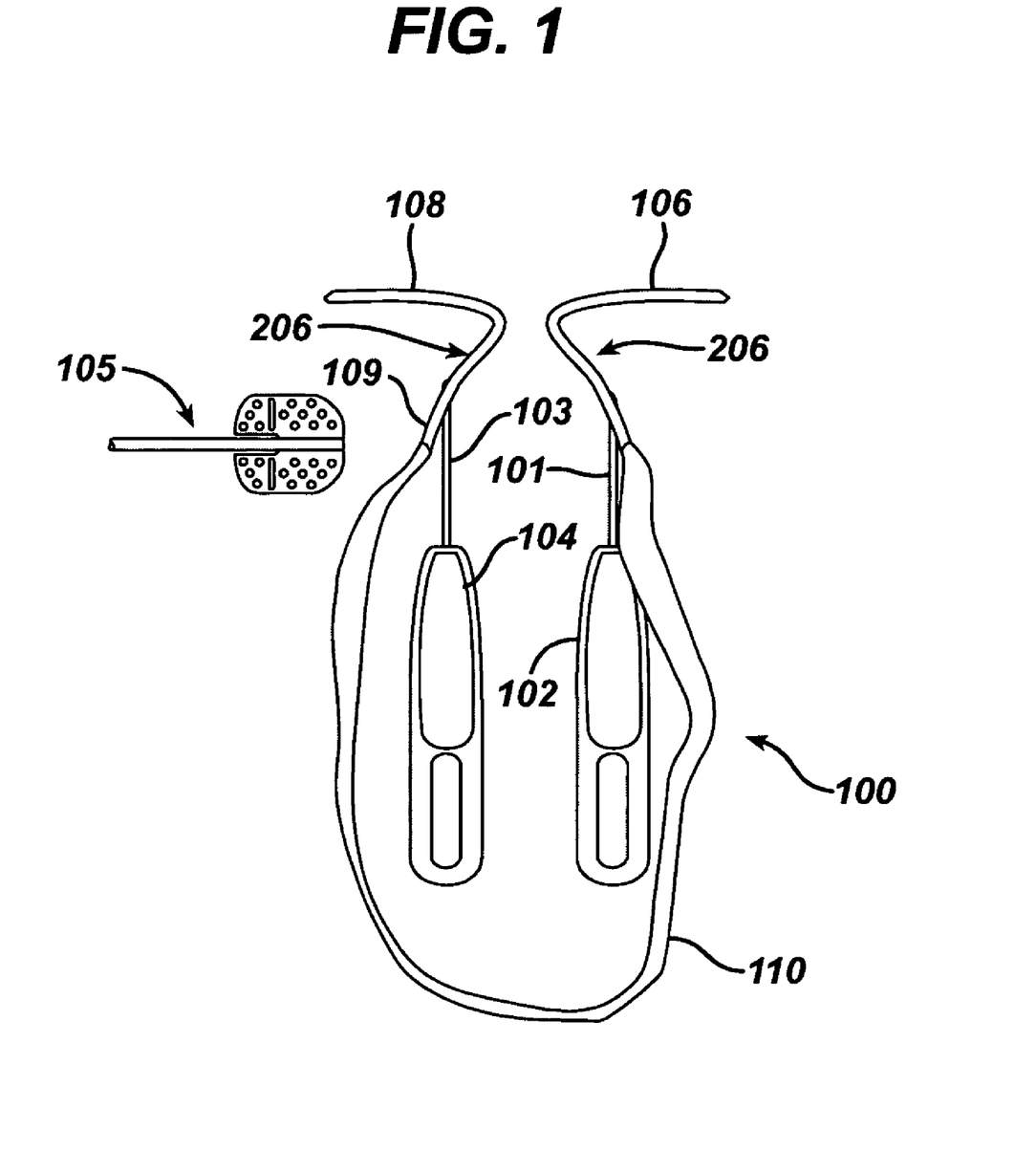
FIG. 1 illustrates a surgical assembly in which the present invention can be employed.
Figure 2:
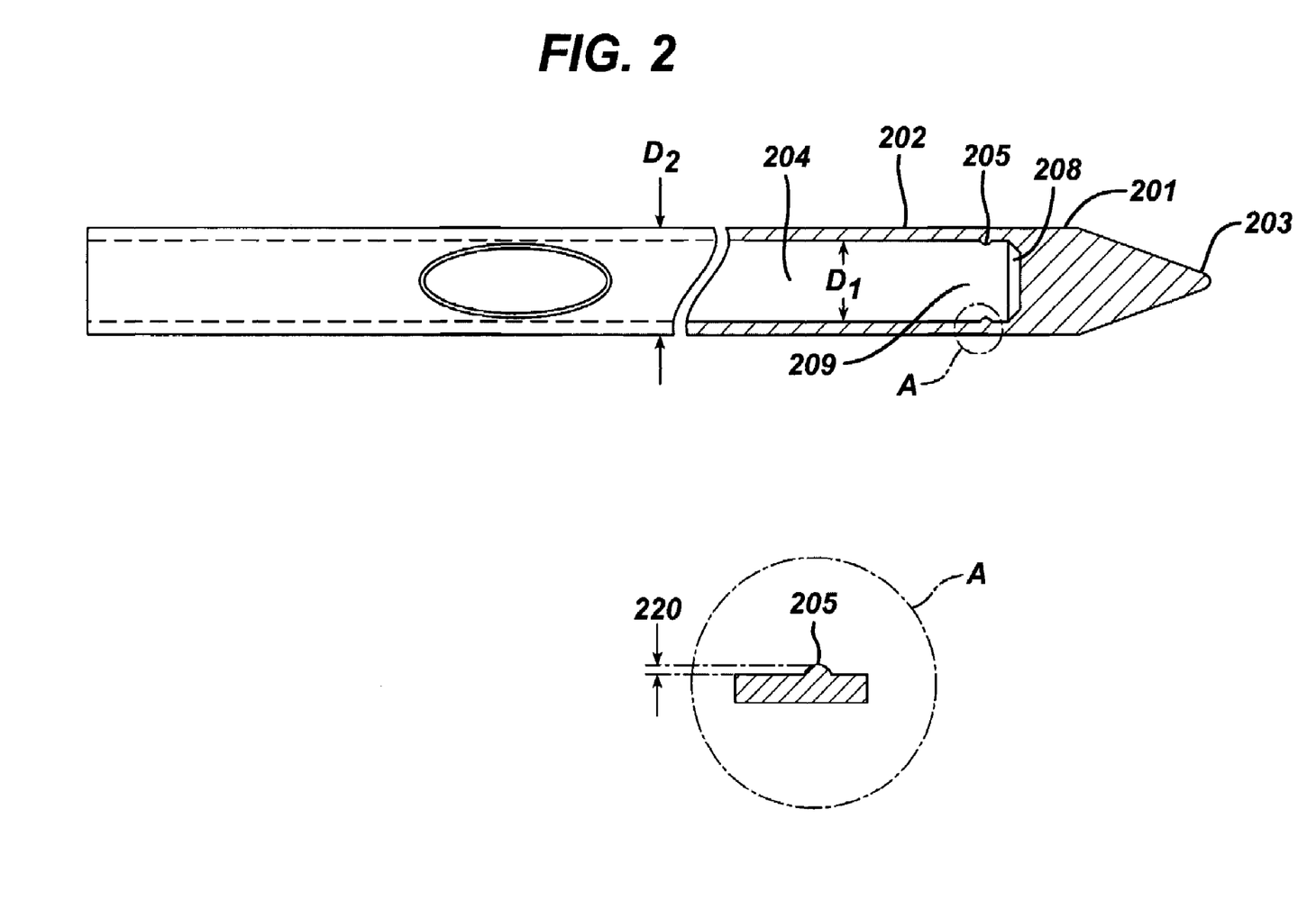
FIG. 2 is a side view of the distal end of a tube element according to the present invention.

Referring now to FIGS. 1-4, as indicated above, the present invention can be employed in the surgical assembly illustrated in FIG. 1. The details of the present invention are further set forth in FIGS. 2-4. FIG. 2 illustrates the distal end region 201 of a tube element 202 having a tissue penetrating distal end 203, an outer diameter D2, and having a channel 204 therein extending from an opening 206 (see FIG. 1) having a diameter D1 along most of its length. A distal end 208 of the channel may further be configured to be substantially complementary to a distal end of the surgical passer described below.

The distal end region 201 of the tube element also includes one or more projections 205 projecting outwardly into the distal end region 209 of the channel 204. In the illustrated embodiment, the one or more projections is a single projection that extends around the outer circumference C1 of the channel. The configuration of this projection is shown in greater detail in sub-portion A of FIG. 2. As illustrated, the projection is curved, having a radius R, the dimensions of which will be described in more detail below. Although shown as having an overall radius, the projection could also simply have radiused corners or any combination of flat and curved surfaces. The tube element is preferably made of plastic, such as high density polypropylene.

Figure 3:
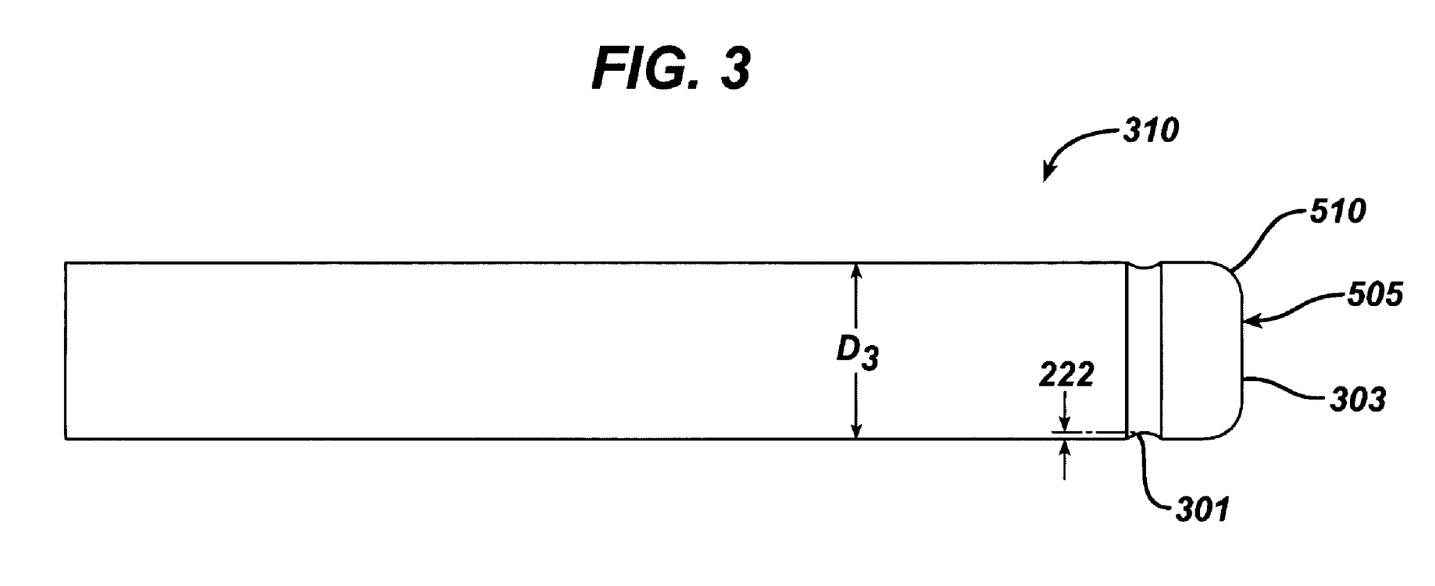
FIG. 3 is a side view of the distal end of a surgical passer according to the present invention.
Figure 5:
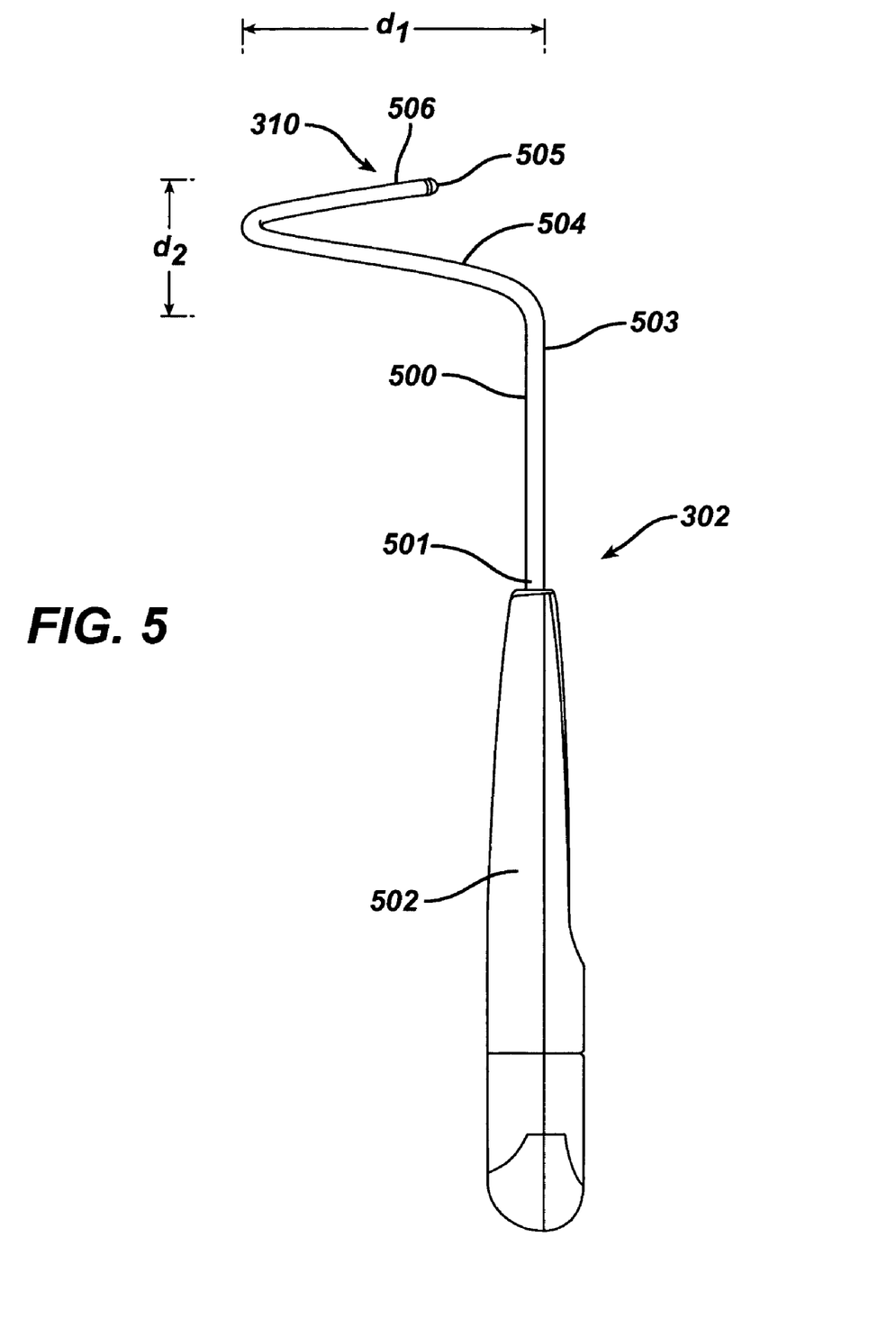
FIG. 5 is a side view illustrating a surgical passer according to the present invention.

FIG. 5 illustrates a surgical passer and FIG. 3 further illustrates the distal end region of the surgical passer 302. In the illustrated embodiment, the surgical passer has a wire portion 500 secured at a proximal end 501 to a handle 502. The wire portion has a substantially straight portion 503, followed by a curved portion 504, and terminates in a free distal end 505. The wire portion may include a second substantially straight portion 506 toward the distal end. In a preferred embodiment, the wire portion is comprised of spring temper stainless steel and has an outer dimension or diameter D3 of approximately 1-6 mm and preferably 2-4 mm. The curved portion 504 is preferably about 127 mm in length, covers a width d1 of approximately 62 mm and a height d2 of approximately 20 mm, with suitable ranges for the latter being approximately 45-80 mm and 10-40 mm respectively.

A distal end region 310 of the surgical passer is shown in greater detail in FIG. 3. The distal end region has at least one recess 301 therein, which in the illustrated embodiment is a single recess extending about the circumference C2 of the surgical passer.

The diameter D3 of the surgical passer is designed relative to the diameter D1 of the tube element so that the surgical passer is insertable within the tube element. The diameter D1 should be sufficiently larger than the diameter D3 so that there is substantially no interference therebetween, or in other words, no press fit condition between the surgical passer and the channel of the tube element that would substantially interfere with the ability to insert the surgical passer within the tube element as described above. In a preferred embodiment, the outer diameter D2 of the tube element is approximately 4.2 mm and its channel dimension or diameter D1 approximately 3.2 mm, whereas the outer diameter D3 of the surgical passer is approximately 3.0 mm. Thus, the diameters are designed such that there will be substantially no interference or press fit between the two elements. However, the term "substantially no interference" should be understood to exclude the interference or engagement caused by the tube element projection that will be described in more detail below, and to also exclude incidental surface contact of the passer and tube during insertion of the surgical passer into the tube element, as their respective configurations requires such contact during insertion and storage.

The term "diameter" has been used above in conjunction with description of a preferred embodiment wherein the surgical passer and tube element has a substantially circular cross-section at the described location. It is to be understood, however, that the surgical passer and/or tube element need not have such a circular cross-section. For example, a given cross-section of the outer peripheral surface 190 of the surgical passer and the peripheral surface 192 defining the channel of the tube element may be of another shape, such as square, hexagon, oval etc. Regardless of shape, the respective dimensions must enable the clearance relative to one another as described above. Further, it is not necessary that the diameter or peripheral surface cross-section remain constant along the length of the surgical passer and/or tube element. The peripheral surface may be such that it is slowly tapered (decreases) along the length, or that a reduced cross-section exists at least along a distal portion of the surgical passer and/or tube element.

Figure 4A:
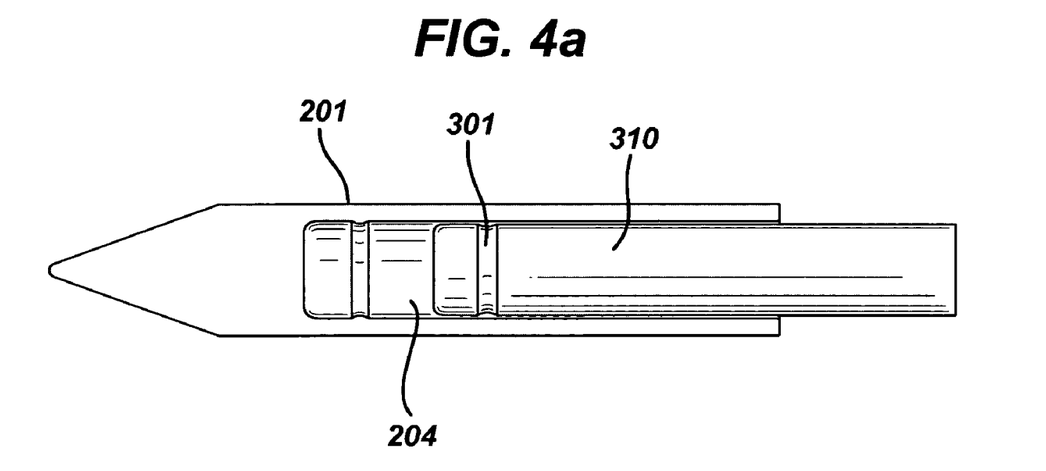
FIGS. 4a and 4b are side views illustrating the distal end of the surgical passer of FIG. 3 inserted within the tube element of FIG. 2 both before and after engagement of the projection and corresponding recess.
Figure 4B:
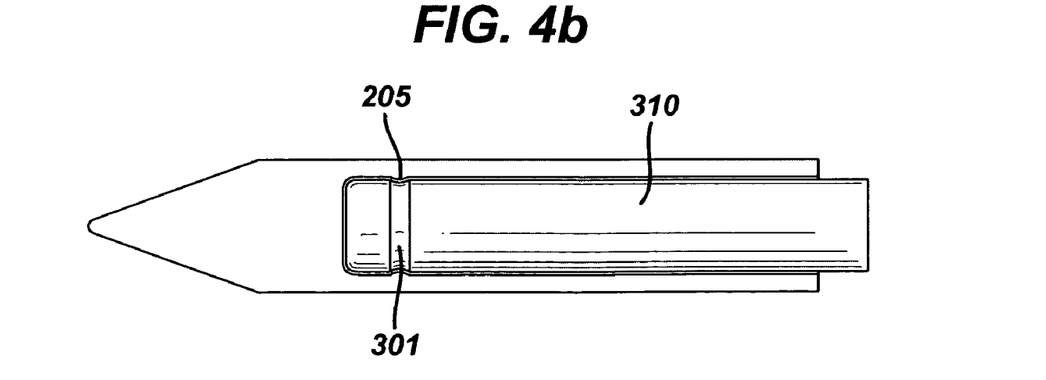

As indicated above, the tube element has a projection 205 and the surgical passer has a recess 301. The projection and recess are designed to engage one another when the surgical passer is inserted into the tube element as shown in FIGS. 4a and 4b, to removably couple the tube element and surgical passer together. They are "removably coupled" in the sense that with a certain amount of force, a user can separate the elements, but this force must exceed that which is normally encountered during use of the instrument as will be described further below. In other words, the tube element and surgical passer must not separate or disengage prematurely from one another while the instrument is being passed through or into the body, and during normal manipulation of the assembly during use. It has been found that the engagement of the projection with the recess must be able to remain engaged under as little as 0.5 pounds of force, and under up to approximately 2 pounds of force, but should release under approximately 8 to 10 pounds of force. In general, disengagement is preferred between 2 and 8 pounds of force with an ideal range between 4 and 6 pounds of force.

In a preferred embodiment, this has been accomplished with a projection 205 having a radius r of approximately 0.5 mm and a height 220 of approximately 0.05 mm in conjunction with a recess having a radius of approximately 0.06 mm and a depth 222 of approximately 0.21 mm. The radius of the projection and recess may vary such that the height and depth preferably fall within the ranges of 0.01-0.5 mm and 0.05-1.0 mm respectively. Further, although the projection and recess are described as having a radius, any other suitable configuration is also possible, such as any combination of curved and/or flat surfaces on either the recess and/or projection.

It should be noted that the radius of the projection and recess are not designed to be substantially complementary to one another, but rather the radius of the projection is intentionally designed to be smaller by a predetermined amount. This is because in addition to performing as an engaging mechanism, the projection and recess must also be sized relative to one another to enable some freedom of movement therebetween to allow effective sterilization of the device in the assembled state. As indicated above, one of the disadvantages of known devices employing a press fit configuration between the surgical passer and tube element is that the press fitting does not allow sterilization gas to effectively reach the distal end of the surgical passer and tube element channel. Thus, pre-assembly was impossible. This meant that the surgeon or surgical staff would need to assemble the tube element and passer in the operating room as the procedure was being performed. Under these circumstances, risk of injury or glove puncture is always possible due to the tissue penetrating distal tip of the tube element.

Even more importantly, assembly in the operating room could lead to inadvertent mismatching of the tube elements with the associated passers or mixing up of which surgical passer/tube element combination was for use on which side of the patient. Use of the wrong instrument on the wrong side of the body could lead to errors during surgery, the most important of which is nicking or puncturing surrounding nerves or organs, such as the critical obturator nerve and vessels. Thus, it is desirable to eliminate as much as possible the potential for human error, and in the present case pre-assembly of the instrument significantly helps in this regard.

Applicants have discovered that this objective can be accomplished with an engagement mechanism as described above that removably couples the surgical passer to the tube element, yet provides sufficient movement therebetween to allow sterilization gasses to adequately enter the region within the channel that is distal or beyond the engagement area. As stated, the projection engages the recess, but is sufficiently smaller than the recess to allow slight movement therebetween. In a preferred embodiment, the depth of the recess is approximately 0.21 mm, whereas the height of the projection is approximately 0.05 mm. It has been demonstrated that such a configuration is adequate to resist separation of the elements during normal use, and allows full sterilization of the assembled instrument.

A further feature of one embodiment of the invention is shown in detail in FIG. 3. At the distal end 505 of the surgical passer, the leading edge 303 is blunt with a radius 510 of preferably a minimum of about 0.1 mm, but could range between 0.05 mm to a full radius forming a half circle. A leading edge with no transition zone could damage the projection as the surgical passer is inserted into the tube element, thereby adversely affecting the ability of the assembly to remain coupled during use. A flat leading edge would also be suitable, such as a peripheral edge having a chamfer at approximately 45+/−30 degrees. Other combinations of chamfered edges or other curvatures may also be suitable so long as they function to assist in moving the distal end of the surgical passer over the projection until the projection engages the recess.

The present invention provides the additional advantage that during assembly of the surgical passer with the tube element, an audible click or the like can be heard, verifying that the two elements are properly disengaged or reengaged if the tubes were accidentally prematurely removed.

A method of using the above-described surgical instrument will now be described in detail. To perform the procedure, the patient is first placed in the dorsal lithotomy position with the hips hyperflexed over the abdomen, and the bladder emptied. Next, the exit points 702 (FIG. 6a) of the instrument through the obturator foramen 707 are marked. A midline incision is then made in the vaginal mucosa 705, and the left and right sides dissected with scissors or the like until it reaches and dissects the obturator membrane.

Figure 6A:
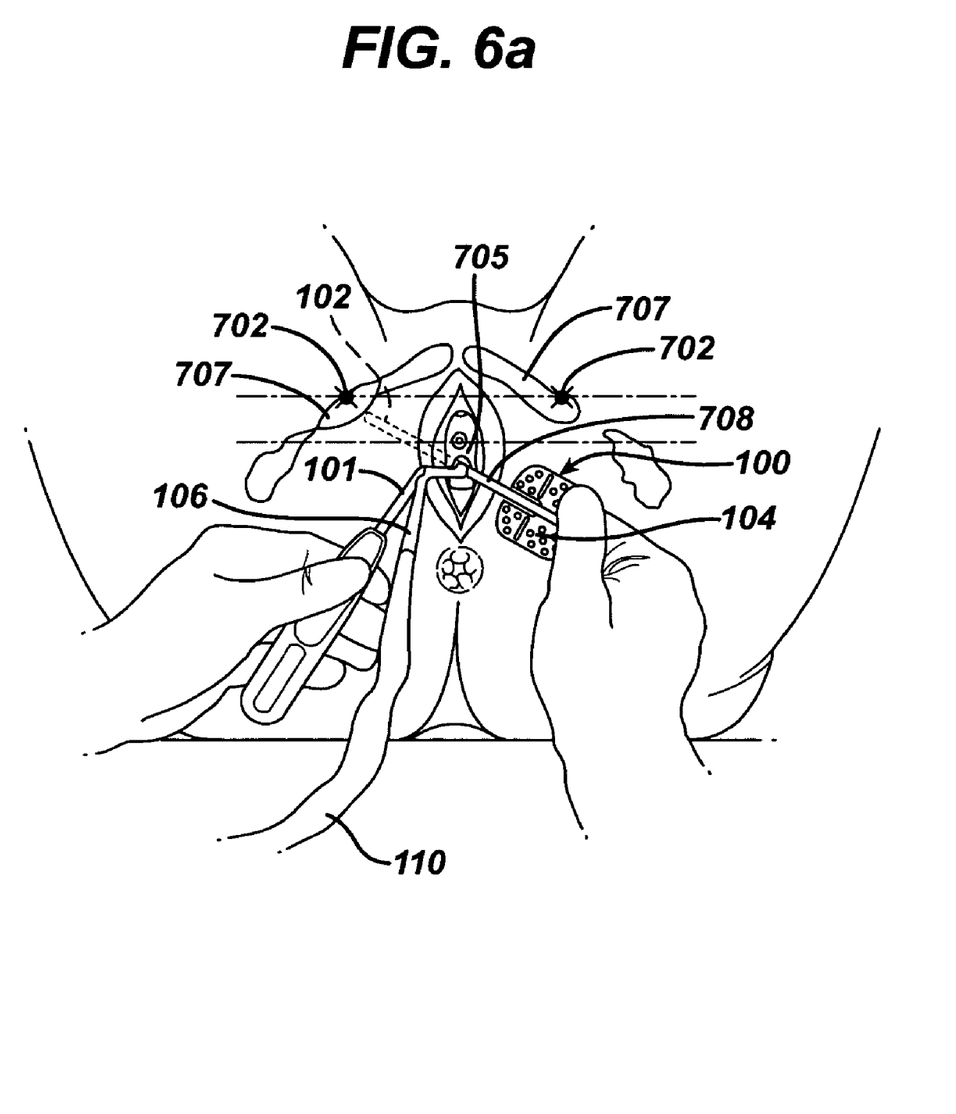
FIGS. 6a-6b illustrate steps in a method using a surgical assembly according to the present invention.

Next, a guide element 100 is inserted as shown in FIG. 6a through the vaginal incision and into the dissected tract until is passes the inferior pubic ramus and enters the opening previously made in the obturator membrane. Extensions 104 of the guide member remains outside the dissected tract and prevent the guide from being over-inserted. The guide may include a C-shaped channel that functions to guide the surgical instrument along the dissected path.

Figure 6B:
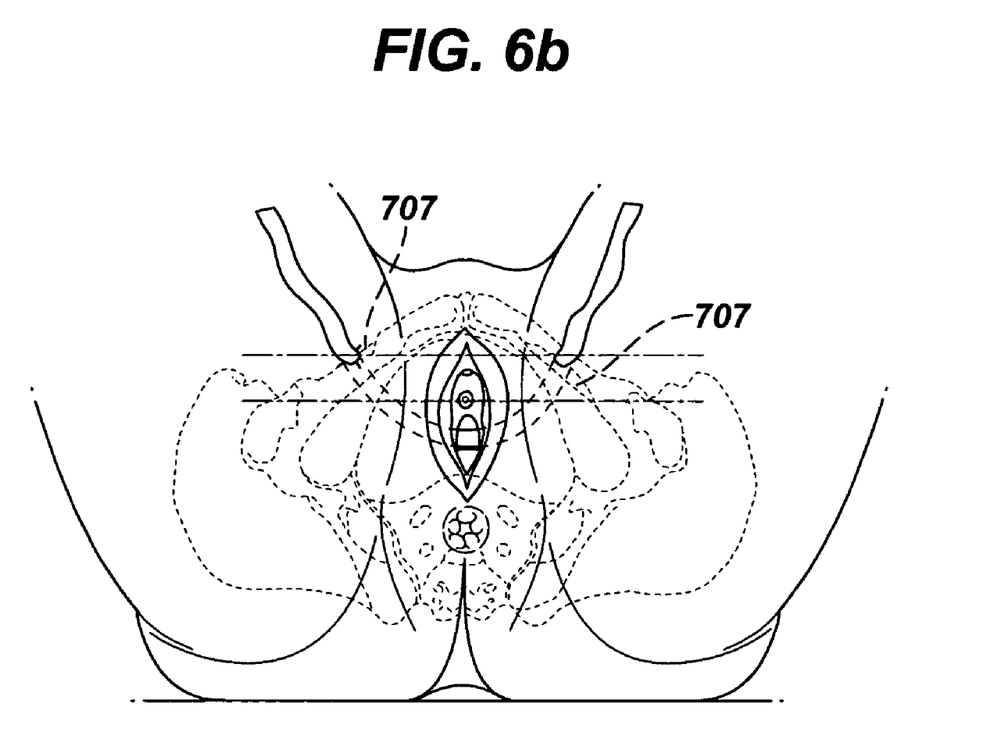

Once the guide element is fully inserted on one side as described above, the pre-assembled surgical passer 101 and tube element 106 for that side of the body is then inserted. The assembly is positioned within the C-shaped stem portion 708 and passed through the dissected tract following the channel of the stem portion of the guide element from the vaginal incision and through the obturator membrane. Once the tip of the assembly traverses the obturator membrane, the guide element is removed. The assembly is rotated the remainder of the way through until the tip emerges from the skin at the exit point. The end of the tube element is then grasped, and the surgical passer reverse rotated to bring it back through the dissected tract and out through the vaginal incision. To accomplish this the tube element is grasped and a sufficient amount of force exerted on the surgical passer to disengage the tube element projection from the surgical passer recess. Thus, the surgical passer and tube element are separated, enabling the passer to be removed via the vaginal incision while the tube element is removed through the obturator foramen. The tube element is pulled through the skin incision until the tape 110 exits the skin incision. The process is then repeated on the patient's other side and the tape adjusted, leaving the tape to form the sub-urethral sling beneath the mid-portion of the urethra as shown in FIG. 6b.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A surgical assembly comprising:
   a surgical passer having a wire portion coupled to a handle, the wire portion having a free distal end, having an outer periphery, and having at least one recess therein in a distal end region;
   a tube element having a proximal end, a tissue penetrating distal end, and a channel extending therein from an opening at the proximal end and defined by an inner periphery, the channel having at least one projection projecting outwardly into the channel in a distal end region thereof;
   wherein the outer periphery of the surgical passer is dimensioned relative to the inner periphery of the channel of the tube element so that the surgical passer is positionable within the tube element, and wherein, when so positioned, the at least one tube element projection engages the at least one surgical passer recess to removably couple the surgical passer to the tube element,
   wherein there is substantially no interference between the surgical passer and tube element other than from the at least one tube element projection.

2. The surgical assembly according to claim 1, wherein the at least one projection is sufficiently smaller than the corresponding recess so as to allow sterilization gas present within the channel to freely pass into a region of the channel distal of the at least one projection.

3. The surgical assembly according to claim 2, wherein the at least one recess has a depth of at least approximately 0.05 mm, and the at least one projection has a height of at least approximately 0.1 mm.

4. The surgical assembly according to claim 3, wherein the at least one recess has a radius of at least approximately 0.1 mm and the at least one projection has a radius of at least approximately 0.1 mm.

5. The surgical assembly according to claim 2, wherein the surgical passer is comprised of stainless steel and the tube element is comprised of a medical grade plastic selected from the group consisting of urethane, polyethylene, and polypropylene.

6. The surgical assembly according to claim 1, wherein a leading edge of the surgical passer has a radius of at least 0.1 mm.

7. The surgical assembly according to claim 1, wherein a leading edge of the surgical passer is chamfered.

8. The surgical assembly according to claim 1, wherein the at least one recess is between 0.5 and 120 mm proximal of the distal end of the surgical passer.

9. The surgical assembly according to claim 1, wherein the at least one recess is a single recess extending around a circumference of the surgical passer, and the at least one projection is a single projection extending around the diameter of the channel.

10. The surgical assembly according to claim 1, wherein the at least one recess is a single recess extending around a circumference of the surgical passer, and the at least one projection is a plurality of projections spaced apart about the diameter of the channel.

11. The surgical assembly according to claim 1, wherein the wire portion of the surgical passer has a contour, and wherein the tube element is configured to follow said surgical passer contour.

12. The surgical assembly according to claim 11, wherein the contour of the surgical passer is substantially helical.

13. A surgical assembly for use in implanting a tape to treat female urinary incontinence comprising;
   a surgical passer having a wire portion coupled to a handle, at least a portion of the wire portion having a curved contour, a free distal end, an outer periphery, and having at least one recess therein in a distal end region;
   a tube element having a proximal end coupled to the tape to be implanted, a tissue penetrating distal end, and a channel extending therein from an opening at the proximal end, the channel having an inner periphery and having at least one projection projecting outwardly into the channel in a distal end region thereof, the tube element having a configuration such that it can be removably positioned over the distal end of the surgical passer and having a contour that substantially follows the contour of the surgical passer;
   wherein when the tube element is removably positioned over the distal end of the surgical passer, the at least one projection on the surgical passer engages the at least one recess in the tube element; and
   wherein there is substantially no interference between the surgical passer and the tube element other than from the at least one tube element projection.

14. The surgical assembly according to claim 13, wherein the at least one projection is sufficiently smaller than the corresponding recess so as to allow sterilization gas present within the channel to pass freely into a region of the channel distal of the at least one projection.

15. The surgical assembly according to claim 14, wherein the at least one recess has a depth of approximately 0.05 mm to 1.0 mm, and the at least one projection has a height of approximately 0.1 to 0.5 mm.

16. The surgical assembly according to claim 13, wherein the at least one recess is a single recess extending around a circumference of the surgical passer, and the at least one projection is a single projection extending around the diameter of the channel.

17. The surgical assembly according to claim 13, wherein the at least recess is a single recess extending around a circumference of the surgical passer, and the at least one projection is a plurality of projections spaced apart about the diameter of the channel.

18. A surgical assembly for implanting a surgical element within a patient's body, the assembly comprising:
   a surgical passer having a wire portion coupled to a handle, at least a portion of the wire portion having a curved contour, having a free distal end, an outer periphery, and having at least one recess therein in a distal end region;
   a tube element having a proximal end coupled to the tape to be implanted, a tissue penetrating distal end, and a channel extending therein from an opening at the proximal end, the channel having an inner periphery and a means for engaging the at least one recess in the tube element to removably couple the tube element to the surgical passer, the means for engaging being capable of withstanding a removal force of approximately 1 to 10 pounds, but allowing sterilization gas present within the channel to freely pass through to the distal end of the channel.

19. The surgical assembly according to claim 18, wherein the means for engaging is at least one projection projecting outwardly into the tube element channel.

20. The surgical assembly according to claim 18, wherein the surgical passer is comprised of stainless steel and the tube element is comprised of a medical grade plastic selected from the group consisting of urethane, polyethylene, and polypropylene.

* * * * *